United States Patent [19]
Kletschka et al.

[11] 4,049,002
[45] * Sept. 20, 1977

[54] FLUID CONVEYING SURGICAL INSTRUMENT

[75] Inventors: Harold D. Kletschka, Minneapolis; Edson D. Rafferty, Excelsior, both of Minn.

[73] Assignee: Bio-Medicus, Inc., Minnetonka, Minn.

[*] Notice: The portion of the term of this patent subsequent to Apr. 30, 1991, has been disclaimed.

[21] Appl. No.: 682,386

[22] Filed: May 3, 1976

Related U.S. Application Data

[60] Division of Ser. No. 597,095, July 18, 1975, Pat. No. 3,980,086, which is a continuation of Ser. No. 446,809, Feb. 28, 1974, abandoned, which is a continuation-in-part of Ser. No. 368,192, June 8, 1973, Pat. No. 3,807,406, which is a continuation of Ser. No. 156,825, June 25, 1971, abandoned.

[51] Int. Cl.² ............................................. A61B 17/32
[52] U.S. Cl. .................................... 128/318; 128/321; 128/276
[58] Field of Search ............... 128/318, 321, 346, 276, 128/240, 254, 329, 305 R, 312

[56] References Cited

U.S. PATENT DOCUMENTS

| | | | |
|---|---|---|---|
| 2,601,513 | 6/1952 | Gladstone | 128/2 R |
| 3,071,402 | 1/1963 | Lasto et al. | 294/64 |
| 3,361,133 | 1/1968 | Kimberley et al. | 128/346 |
| 3,367,336 | 2/1968 | Eizenberg | 128/321 |
| 3,495,593 | 2/1970 | Snyder | 128/309 |
| 3,561,448 | 2/1971 | Peternel | 128/346 |
| 3,606,681 | 9/1971 | Rogers et al. | 128/318 X |
| 3,749,090 | 7/1973 | Stewart | 128/240 |
| 3,807,406 | 4/1974 | Rafferty et al. | 128/318 |

Primary Examiner—Robert W. Michell
Assistant Examiner—Henry J. Recla
Attorney, Agent, or Firm—Merchant, Gould, Smith, Edell, Welter & Schmidt

[57] ABSTRACT

A surgical instrument of scissors configuration having one or more suction and spraying openings disposed at the functional end thereof, the openings communicating with a fluid conduit which is carried by and movable with one or both of the instrument handles or manipulating means. Movable conduit extensions selectively locate the suction and spraying openings in areas adjacent the scissors functional ends.

10 Claims, 22 Drawing Figures

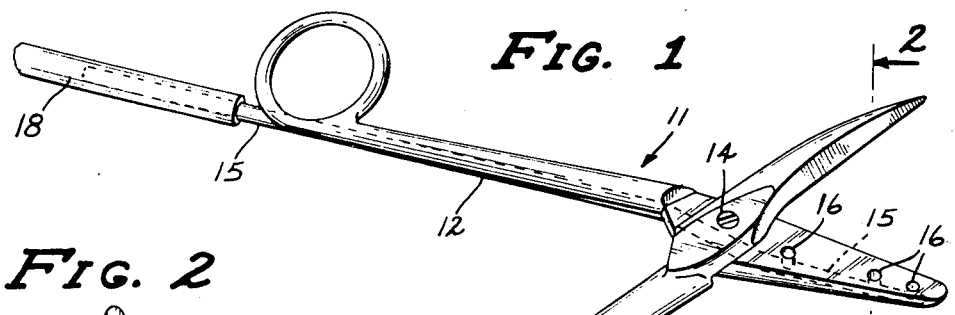
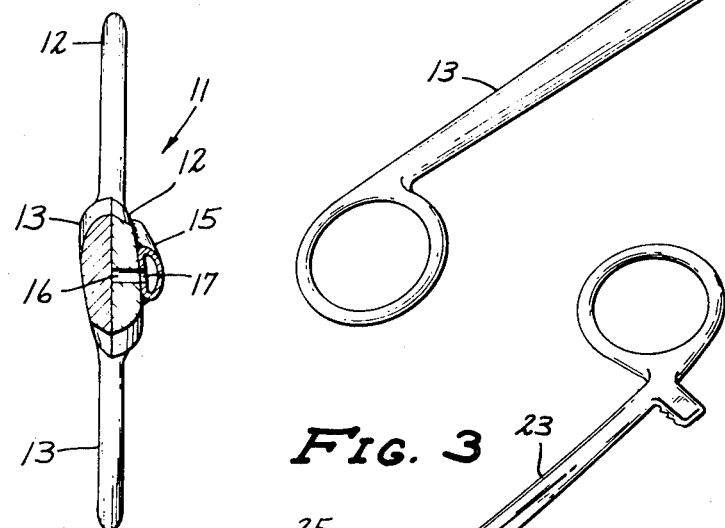
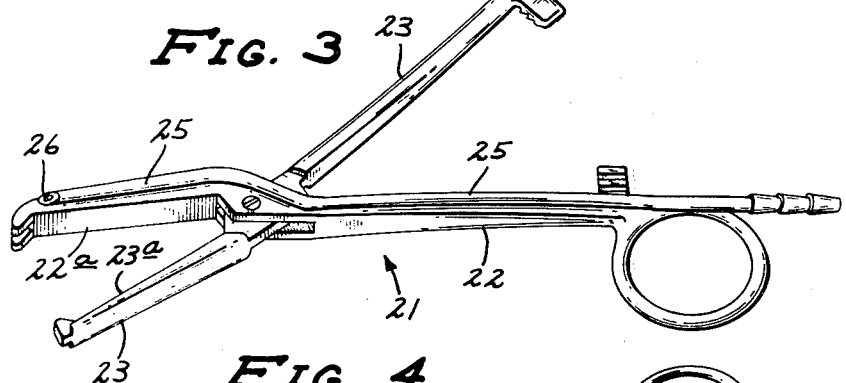
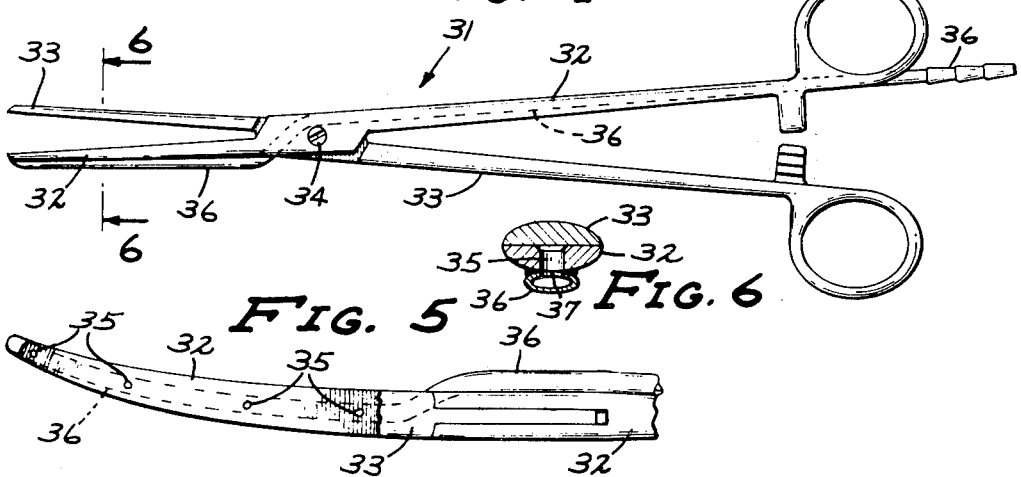

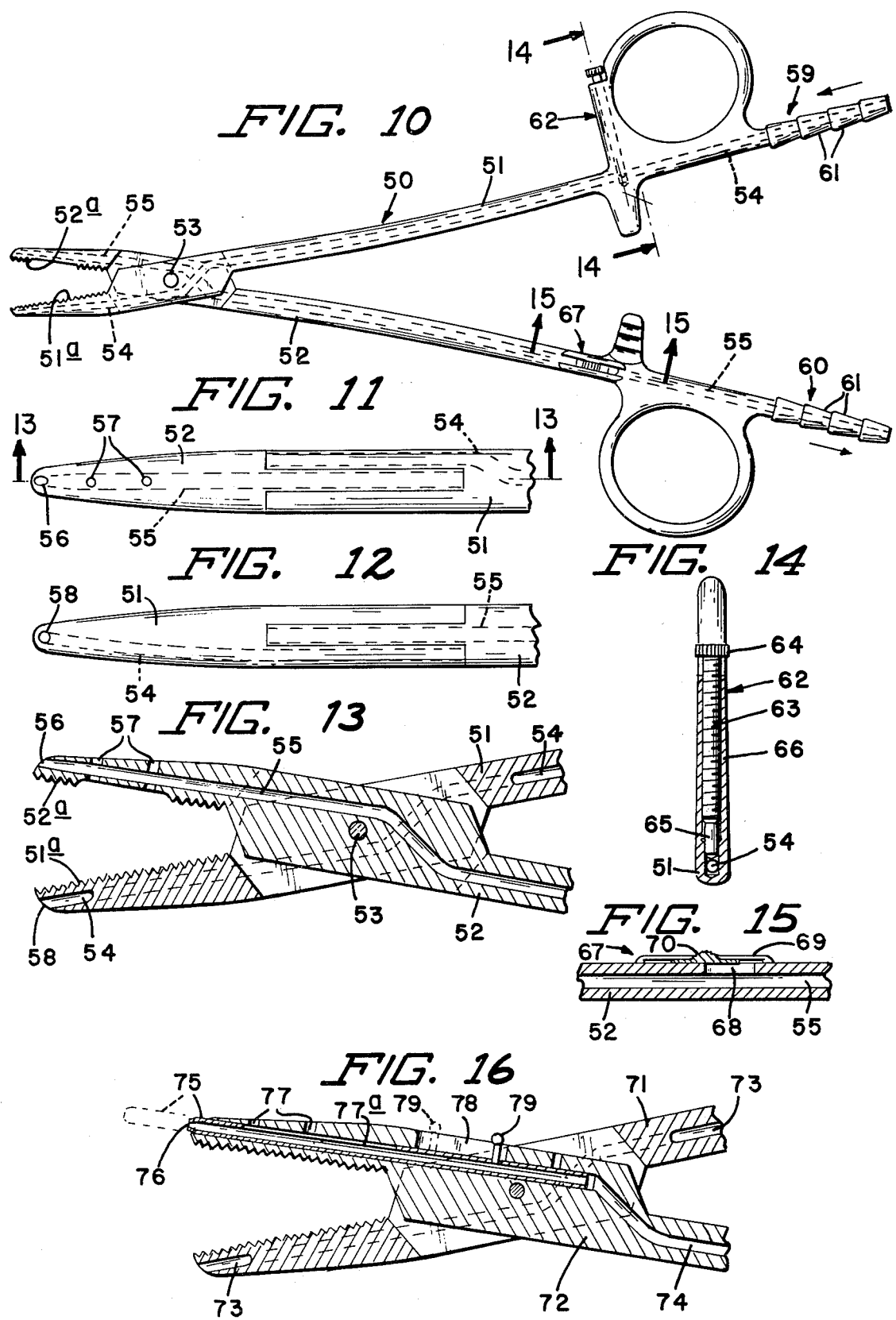

FLUID CONVEYING SURGICAL INSTRUMENT

This is a Division of application Ser. No. 597,095, filed July 18, 1975 now Pat. No. 3,980,086, which is a Continuation of application Ser. No. 446,809, filed Feb. 28, 1974 of Harold D. Kletschka and Edson H. Rafferty for "Fluid Conveying Surgical Instrument," now abandoned which is a Continuation-In-Part of application Ser. No. 368,192, filed June 8, 1973, issued Apr. 30, 1974, under U.S. Pat. No. 3,807,406, which is a Continuation of application Ser. No. 156,825, filed June 25, 1971 of Harold D. Kletschka and Edson H. Rafferty for "Surgical Instrument with Suction Device" now abandoned.

BACKGROUND

1. Field of the Invention

The invention relates generally to surgical instruments, and is specifically directed to an instrument of generally scissors configuration which includes suction and spraying means for cleansing and removing fluid and/or fumes from a surgical area. As used herein, the term scissors refers to the manipulating action of the instrument rather than the cutting or shearing action of the functional end of the instrument.

2. Background of the Invention

One problem encountered in the performance of surgical operations is the removal of blood and other body fluids, and sometimes fumes, from the area in which surgery is undertaken. The presence of such fluids may be the direct result of incision, or there may have been an accumulation prior to entry into the area. Fumes can sometimes be a problem also, such as when a Bovey current is being used. In any such situation, it is ordinarily necessary that such fluids or fumes be removed as quickly as possible to permit the surgeon to carry out his tasks with the least possible obstruction.

Another related problem encountered in surgery is the presence of blood or other material on and about tissue in the surgical area and which cannot be removed by suction alone. Such material tends to adhere to the tissue and impairs the surgeon's view of the surgical area.

One solution to these problems has been the provision of a probe or similar device which is connected to a vacuum source and is capable of aspirating body fluids from the surgical area. However, when the surgeon is using scissors, forceps, or the like in his operative tasks, it is necessary either that the suction device be manipulated by a surgical assistant, which is often impossible due to space limitations; or, that the surgeon change instruments as often as the accumulation of fluid becomes a problem.

SUMMARY

Our invention enables the surgeon to perform the normal surgical tasks as well as the simultaneous or separate cleansing of tissue and suction removal of accumulated fluids from the surgical area with a single surgical instrument. The instrument is of scissors configuration and includes one or more aspirating or suction openings at the functional end of the instrument which communicates with a fluid conduit carried by and movable with one or both of the instrument handles or manipulating means. The conduit is connected to a source of vacuum or liquid under pressure thus permitting the surgeon to cleanse the area or effect the removal of body fluids simply by placing the instrument openings adjacent to the surgical area.

BRIEF DESCRIPTION OF THE DRAWINGS

FIG. 1 is a perspective view of surgical scissors embodying the inventive principle, the scissors being shown in an open position;

FIG. 2 is a sectional view of the surgical scissors taken along the line 2—2 of FIG. 1, with the scissors in a closed position;

FIG. 3 is a perspective view of a surgical clamp embodying the inventive principle, the clamp being shown in an open position;

FIG. 4 is a top plan of an alternative surgical clamp shown in an open position;

FIG. 5 is an enlarged fragmentary view in elevation of the surgical clamp of FIG. 4; and portions thereof broken away;

FIG. 6 is an enlarged sectional view of the surgical clamp taken along the line 6—6 of FIG. 4, the jaws of which are shown in a closed position;

FIG. 10 is a top plan view of an alternative needle holder instrument shown in an open position;

FIG. 11 is an enlarged elevational view of the functional end of the instrument shown in FIG. 10;

FIG.12 is an enlarged elevational view showing the side opposite that shown in FIG. 11;

FIG. 13 is an enlarged fragmentary top plan view along the line 13—13 of FIG. 12;

FIG. 14 is an enlarged fragmentary view of the fluid control along the line 14—14 of FIG. 10;

FIG. 15 is an enlarged fragmentary view of the vacuum control along the line 15—15 in FIG. 10;

FIG. 16 is an enlarged top plan view of the jaw section of an alternative needle holder instrument with a conduit extension;

DESCRIPTION OF THE PREFERRED EMBODIMENTS

Figure 7:
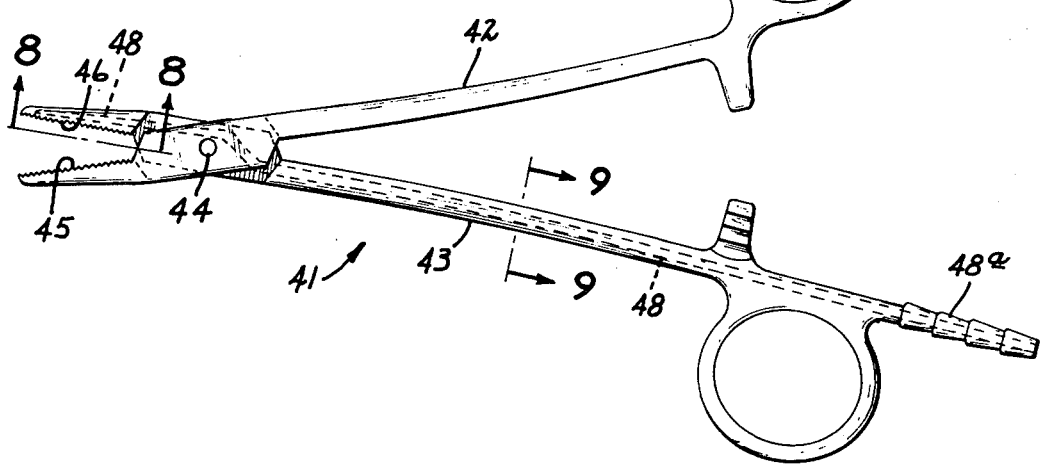
FIG. 7 is a top plan of a needle holder instrument shown in an open position.

Referring initially to FIGS. 1 and 2, a surgical instrument of scissors configuration is represented generally by the numeral 11, and is shown to comprise a pair of elongated members 12, 13, each of which has blade end and a handle end, sometimes referred to herein as manipulating means. Elongated members 12 and 13 are pivotally connected at an intermediate point by a screw or rivet 14, or other pivotal means, in a manner so that the respective blade ends thereof may co-act to perform a surgical cutting or dissecting operation by relative movement of the handle portions. Although FIGS. 1 and 2 show a surgical scissors, the term scissors configuration is often used herein to refer to the general type of pivotally connected instrument rather than any cutting or shearing action performed thereby.

A fluid conduit 15 has one side conforming generally to the shape of elongated member 12, and is affixed to the outer face of member 12 over its length for movement therewith.

The conduit 15 is shown in FIG. 2 to have a flattened cross section, but this is not a necessary feature of the device. It will also be noted that the conduit 15 may be integrally formed within the elongated member 12. Also, it may be desired for some applications to provide conduits for both elongated members 12, 13. A plurality of bores 16 (three are shown in FIG. 1) extend through the blade portion of elongated member 12 from the inner face to the outer face thereof, and communicate with conduit 15 through aligned openings 17 formed therein. In some instruments, it may be desirable to have only one opening on the instrument end portion, and for other instruments it may be desirable to have openings which open on the inner, outer, side or end faces of the instrument.

The opposite end of conduit 15 projects beyond the associated handle portion, as shown in FIG. 1, and is adapted for connection to a vacuum source through a flexible tube 18. For some uses, the conduit 15 may be connected to source of fluid under pressure to be dripped from the openings 17 for washing purposes. The source of vacuum of fluid under pressure is sometimes broadly referred to herein as a source of fluid pressure differential. Also, it may be desirable to provide one of the members 12, 13 with a conduit connected to a vacuum source where the other member has a conduit connected to a fluid pressure source so that the washing fluid may be simultaneously flushed out and removed.

In FIG. 3, a surgical instrument 21 comprises a pair of pivotally connected elongated members 22-23, the functional ends of which are shaped to provide a clamping or forcep-type function. A fluid conduit 25 is affixed to or made part of elongated member 22 over its length, and terminates in one or more openings 26 immediately adjacent the forceps tip or other desired location. The inner faces 22a and 23a of the members 22, 23 are provided with gripping striations, as shown in FIG. 3.

FIGS. 4-6 disclose an alternative clamp 31, which again comprises a pair of elongated members 32, 33 which are pivotally connected at an intermediate point by a screw or rivet 34, or other pivotal means. As best seen in FIG. 5, the functional ends of elongated member 32, 33 are curved to facilitate the clamping, grasping or dissecting function in areas which are difficult to reach, although such ends may obviously be of straight or other configuration.

A plurality of bores 35 are formed in the functional tip of elongated member 32, opening on the inner face thereof in a manner similar to the bores 16 of instrument 12. One or more bores 35 may be suitably located at various positions as noted above in connection with instrument 12. A fluid conduit 36 is also affixed to elongated member 32 for movement therewith, and fluid communication is established with the bores 35 through openings 37 formed therein.

Figure 8:
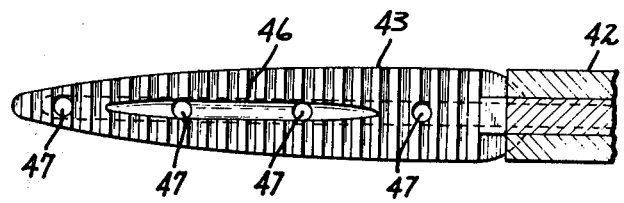
FIG. 8 is an enlarged sectional view taken along the line 8—8 of FIG. 7.
Figure 9:
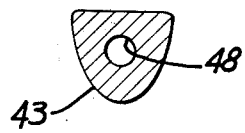
FIG. 9 is an enlarged sectional view taken along the line 9—9 of FIG. 7.

FIG. 7-9 disclose another embodiment of our invention which comprises a surgical instrument commonly referred to as a needle holder 41. The needle holder 41 is also constructed in a manner referred to herein as a generally scissors configuration, and comprises a pair of elongated members 42, 43 which are pivotally connected at an intermediate location by means of a screw 44 or other pivotal connecting means.

The functional ends of members 42, 43 are provided with serrated or striated inner faces 45, 46 to facilitate firm gripping of a needle, not shown. A plurality of bores 47 are shown opening into the face 46, although only one bore may be desired for some applications or several bores opening at different locations on the instrument end portion may be desired in still other instrument designs. A fluid conduit 48 is formed within the member 43, as best shown in FIG. 9, and is arranged to provide fluid communication with the bores 47. Although this location of the fluid conduit is shown in association with the needle holder, the same fluid conduit location could be used in the other instrument as well. The projecting end portion 48a of conduit 48 is adapted to permit connecting with a vacuum source, as noted above, to provide for the removal of blood and other fluids.

FIGS. 10 through 15 show another embodiment of our invention which comprises a needle holder instrument 50. The needle holder 50 has a generally scissors configuration, and comprises a pair of elongated members 51 and 52 held together at a pivot point by a screw and nut 53. The inner faces 51a and 52a of elongated members 51 and 52 respectively have serrations for holding a needle when the elongated members are in a closed position. In the configuration of FIG. 10, fluid conduits 54 and 55 extend through the elongated members 51 and 52 respectively. Connectors 59 and 60 are attached to the ends of elongated members 51 and 52 for attachment of flexible hoses and the like to the fluid conduits 54 and 55. Tapered shoulders 61 are provided on each of connectors 59 and 60 for holding a flexible hose (not shown) in place on the connectors 59 and 60. Fluid conduit 54 terminates in an opening 58 at the tip of elongated member 51, and fluid conduit 55 terminates in an opening 56 near the tip of elongated member 52, see FIGS. 11-13. In addition, bores 57 extend transversely through a portion of elongated member 52 from its outer surface to the conduit 55. In the configuration shown in FIGS. 10-13, there are two bores 57 but other numbers may also be used. It is the purpose of the multiplicity of bores 57 in combination with opening 56 to provide a continuous flow of liquid into or out of passageway 55 even when one or more or these openings or bores are blocked by tissue.

The use of two conduits 54 and 55 in the needle holder instrument 50 allows cleansing fluid under pressure to be transmitted to the surgical area by one of the the conduits and a vacuuming operation through the other conduit. To control the flow of liquid under pressure through conduit 54 in needle holder 50, a flow control valve 62 is provided on elongated member 51. As is shown in detail in FIG. 14, flow control valve 62 consists of a screw member 63 which advances through a threaded housing 66. A barrier pin 65 attached to the base of screw member 63 allows the conduit 54 to be partially or totally blocked as the screw 63 is advanced. A thumb control member 64 at the end of screw member 63 allows it to be advanced by a simple hand motion. Friction fit between the screw member 63 and the housing 64 maintains the screw 63 in its pre-selected position.

A vacuum control valve 67 has been provided on elongated member 52 to control the amount of vacuum supplied through conduit 55. As is shown in detail in FIG. 15, vacuum control valve 67 comprises a slide rail 69 attached to elongated member 52 and a slide member 70 which moves within the slide rail 69. As the slide member 70 moves within rail 69 it covers an opening 68 which extends from the outside of elongated member 52 to the conduit 55. By selectively positioning slide member 70 over the opening 68, the amount of vacuum which is drawn through the plurality of openings at the end of conduit 55 may be controlled. A friction fit between slide member 70 and rail member 69 allows the slide member 70 to be maintained in the selected position.

FIG. 16 shows an alternative embodiment for the blade end of needle holder 50. An extension tube 75 is inserted in fluid conduit 74 near the tip of elongated member 72. Extension tube 75 has an opening 76 in its end and the opening 76 is located within the leg member 72 when the extension tube is in its retracted position. In this retracted position, an opening 77a in extension tube 75 is in register with bores 77 in elongated member 72. This allows the bores 77 to perform their fluid supply or vacuum function when extension tube 75 is retracted. The opening 77a is of such length longitudinally of the extension tube 75 that it is also in register with bores 77 when extension tube 75 is in its extended position. If it is desired to provide maximum suction through extension tube opening 76 in its extended position, the opening 77a may be shaped and arranged so that it is out of register with bores 77 when the tube 75 is fully extended.

To move extension tube 75 from its retracted position to an extended position, a thumb member 79 is attached to extension tube 75. Thumb member 79 protrudes through a slot 78 in leg member 72 and has a portion exposed such that a person may merely slide thumb member 79 forward in slot 78 to advance the extension tube 75. A friction fit between thumb member 79 and the sides of slot 78 allow the extension tube 75 to be held in the selected position. While the conduit 73 is not shown with an extension tube, it would also be possible to insert an extension tube into conduit 73. The use of extension tube 75 or others like it allow the cleansing liquid which is carried in conduit 74 or the vacuum source to which it is attached to be extended to an area removed from the tip of elongated member 51. Such an operation may be desirable where a pool of liquid or tissue to be cleansed is slightly removed from needle which is grasped by the needle holder 50.

Figure 17:
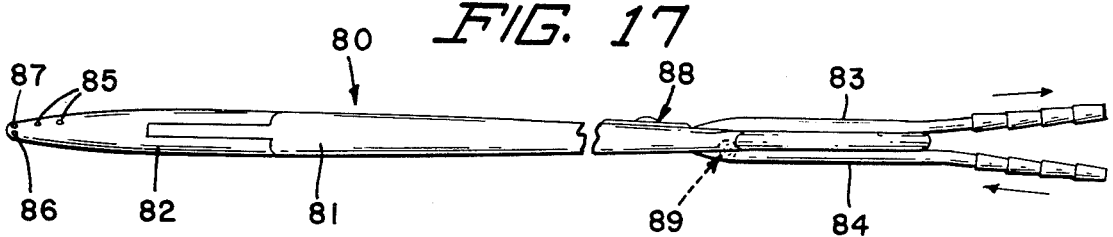
FIG. 17 is an elevational view of an alternative needle holder instrument.
Figure 18:
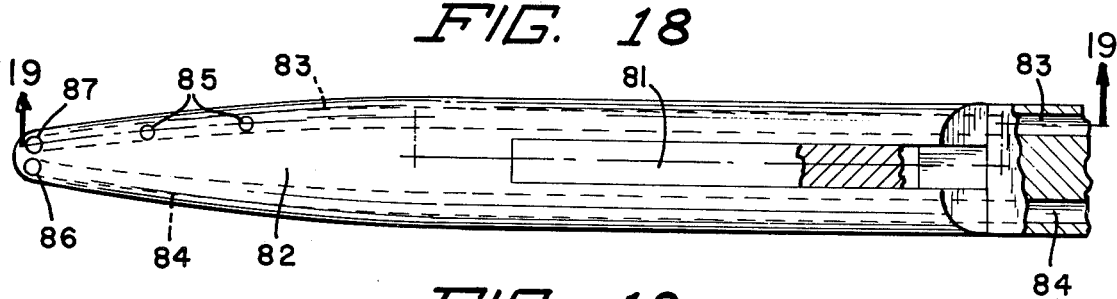
FIG. 18 is an enlarged partial fragmentary view in elevation of the functional portion of the instrument shown in FIG. 17.
Figure 19:
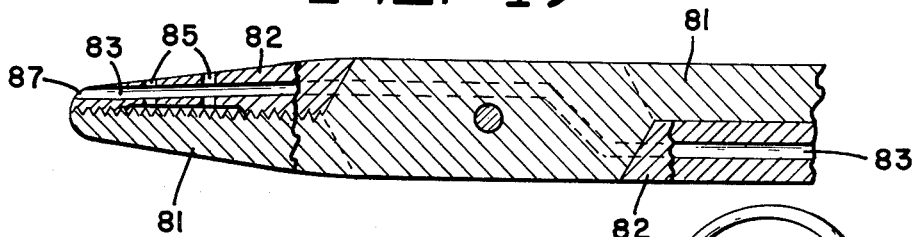
FIG. 19 is an enlarged sectional view of the surgical instrument taken along the line 19—19 of FIG. 18, the jaws of which are shown in closed position.

FIGS. 17 through 19 show a needle holder instrument 80 which incorporates an alternative embodiment of the present invention. Needle holder 80 comprises two elongated members 81 and 82 pivoted at a common point near the tips of the elongated members. Two conduits 83 and 84 are provided on one of the elongated leg members 82. As is shown in detail in FIG. 18, conduit 83 terminates in an opening 87 near the tip of elongated member 82 and also connects with two bores 85 which extend transversely through a portion of elongated member 82. Conduit 83 extends along one side of elongated member 82 and the bores 85 are located off-center on the elongated member. Conduit 84 extends along the opposite side of elongated member 82 and terminates in an opening 86 located at the tip of elongated member 82 adjacent to opening 87. By using two conduits on one elongated member of the needle holder 80, a cleansing operation and a vacuuming operation can be performed in a very small area near the tip of the instrument. This type of operation is particularly useful in that the liquid supplied for cleansing purposes by one conduit can be immediately vacuumed from the area by the second conduit. To control the flow of liquid through conduit 84, a fluid flow valve 89 is provided on elongated member 82. To control the amount of vacuum provided at the end of the conduit 83, a vacuum control valve 88 is provided on elongated member 81. These valves are shown in FIG. 17 and are similar to the valves 62 and 67. As is noted in detail in FIG. 19, the bores 85 which communicate with conduit 83 from the exterior surface of elongated member 82 extend all the way through elongated member 82 to the interior serrated portion. This allows the cleansing or vacuuming function to be performed either near the interior or exterior sides of elongated member 82. Such a dual function is often desirable where either the interior or exterior openings to bores 85 are blocked by tissue or the like.

Figure 20:
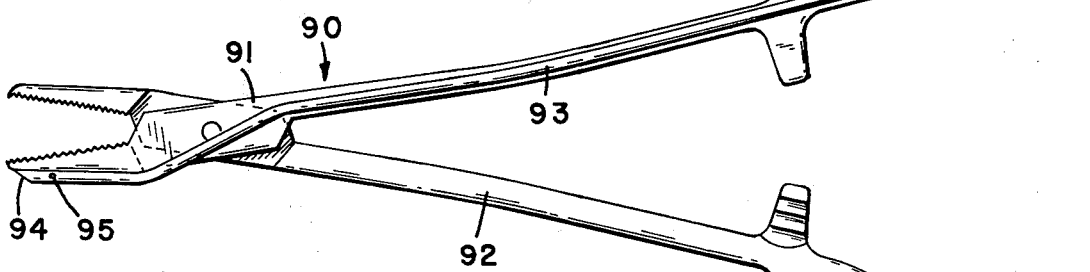
FIG. 20 is a perspective view of an alternative needle holder instrument shown in an open position.
Figure 22:
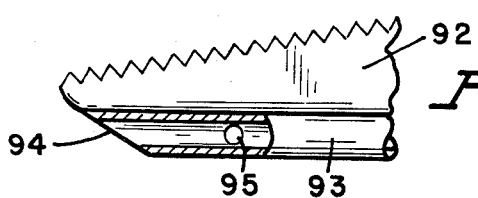
FIG. 22 is an enlarged partial fragmentary view of the jaw tip of the needle holder instrument shown in FIG. 20.
Figure 21:
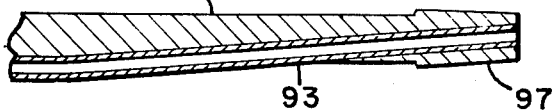
FIG. 21 is an enlarged sectional top plan view of the needle holder instrument along line 21—21 in FIG. 20.

FIGS. 20-22 show a needle holder 90 which utilizes a conduit 93 extending generally along the outside of an elongated member 91. To anchor the exterior conduit 93 firmly to the elongated member 91, conduit 93 extends through a portion of elongated member 91 near the handle of the instrument. A connector 97 is attached to elongated member 91 near the handle for attaching a flexible tube, not shown, to the conduit 93. As is shown in detail in FIG. 21, where the conduit 93 enters the elongated member 91 it is still an integral tubing and does not terminate in a simple bore within the elongated member 91. This use of a continuous conduit instead of a conduit in combination with an interior bore in elongated member 91 provides a smoother interior surface for the conduit and reduces the chances of clogging or the accumulation of contaminating materials.

Conduit 93 takes the form of a circular tube, terminating in an end opening 94 which is disposed proximate the tip or extreme functional end of elongated member 91. The opening 94 lies in and is defined by an oblique plane which transects the conduit tube 93, so that opening 94 is elliptical in shape and of greater cross sectional size than the perpendicular cross section of the conduit tube 93. As shown, the oblique plane is inclined toward the extreme end of elongated member 91, so that the end of conduit tube 93 tapers relative to elongated member 91.

Spaced from end opening 94 are a pair of transverse openings 95, which are formed through the wall of conduit tube 93. The transverse openings are of lesser cross sectional size than the end opening 94, and they are preferably disposed in transverse alignment, thus being respectively accessible from opposite sides of elongated member 91.

It will be appreciated from the foregoing that each of the respective devices 11, 21 and 31 are capable of removing body fluids or fumes and the like from a surgical area in addition to incision, clamping, dissecting or other useful surgical functions by simple exposure of suction openings to such fluids, fumes or gases. Thus, the surgeon is capable of keeping the surgical area continuously clean without help or hindrance from an assistant and without changing instruments. This helps to remove the hindrance of additional hands in the surgical incision area and also permits the use of a freed hand for other purposes.

What is claimed is:

1. A surgical instrument of scissors type configuration, comprising:
   a. first and second elongated members of essentially the same length, each having a manipulating end and a functional end, said functional ends having opposed impermeable inner faces and distal outer faces, said inner faces being substantially adjacent each other in the closed position, the first and second elongated members being pivotally connected at an intermediate point and arranged so that the functional ends together provide a surgical function upon relative movement of said manipulating ends;
   b. first and second fluid conduit means respectively associated with the first and second elongated members, each of said conduit means terminating in an opening in the distal outer face of the associated elongated member at the extreme functional end thereof;
   c. said first fluid conduit means being adapted for connection to a source of negative fluid pressure;
   d. and the second fluid conduit means being adapted for connection to a source of positive fluid pressure.

2. The surgical instrument defined by claim 1, wherein each conduit means defines a passageway formed within at least a portion of its associated elongated member, and further comprising a fluid connector member affixed to each elongated member and communicating with the associated passageway, said connector members being adapted for connection to the sources of fluid pressure.

3. The surgical instrument defined by claim 1, wherein the functional ends of the first and second elongated members comprise clamping members constructed and arranged to perform a forceps-type or clamping function.

4. The surgical instrument defined by claim 1, wherein the functional ends of the elongated members comprise gripping portions constructed and arranged to perform a needle-holding function.

5. The surgical instrument defined by claim 1, wherein the point at which the first and second elongated members are pivotally connected is disposed nearer said functional ends than said manipulating ends.

6. The surgical instrument defined by claim 1, further comprising vacuum control means associated with said first fluid conduit means for controlling the amount of negative fluid pressure differential across the opening in said first fluid conduit means at said functional end.

7. The surgical instrument defined by claim 6, wherein said vacuum control means comprise:
   a. a slot-like opening formed in the first elongated member and communicating with said first fluid conduit means; and
   b. a slide member movably mounted over said slot-like opening for partially covering said slot-like opening to control the amount of negative fluid pressure conveyed to the opening in said first conduit means at said functional end of the first elongated member, said slide member movable in response to urging by finger force.

8. The surgical instrument defined by claim 1 and further comprising pressure control means associated with said second fluid conduit means for regulating the transmission of positive fluid pressure from its source to the opening in said second fluid conduit means at the functional end of said second elongated member.

9. The surgical instrument defined by claim 8 wherein said pressure control means are attached to said second elongated member and are operable by finger force.

10. A surgical instrument of scissors type configuration, comprising:
    a. first and second elongated members of essentially the same length, each having a manipulating end and a functional end, said functional ends having opposed inner faces and outer faces, said inner faces being substantially adjacent each other in the closed position, the first and second elongated members being pivotally connected at an intermediate point and arranged so that the functional ends together provide a surgical function upon relative movement of said manipulating ends;
    b. fluid conduit means associated with at least one of the first and second elongated members, the conduit means terminating in at least one fluid opening disposed on the inner face of the first elongated member, and at least one fluid opening disposed on the outer face of the first elongated member;
    c. the fluid conduit means being adapted for connection with a source of fluid pressure.

* * * * *